United States Patent [19]

Fages et al.

[11] Patent Number: 5,723,012
[45] Date of Patent: Mar. 3, 1998

US005723012A

[54] USES FOR A CURRENT OF SUPERCRITICAL CARBON DIOXIDE AS AN ANTIVIRAL AGENT

[75] Inventors: Jacques Fages, Portet Sur Garonne; Patrick Frayssinet, Saiguede; Gilbert Bonel, Toulouse, all of France

[73] Assignee: Bioland, Toulouse, France

[21] Appl. No.: 576,565

[22] Filed: Dec. 21, 1995

Related U.S. Application Data

[63] Continuation-in-part of Ser. No. 163,775, Dec. 9, 1993, abandoned.

[30] Foreign Application Priority Data

Jun. 13, 1995 [FR] France ............................ 95 07266

[51] Int. Cl.$^6$ .............................. A61F 2/28; A61F 2/54
[52] U.S. Cl. ..................................... 623/16; 623/66
[58] Field of Search ................. 623/16, 66; 424/422, 424/423

[56] References Cited

U.S. PATENT DOCUMENTS 4,776,173  10/1988  Kamarei et al. ..................... 62/63

FOREIGN PATENT DOCUMENTS

| 0 603 920 A1 | 6/1994 | European Pat. Off. |
| 2695140 | 3/1994 | France. |
| WO 93/17724 | 9/1993 | WIPO. |
| 9403590 | 2/1994 | WIPO. |

*Primary Examiner*—Debra S. Brittingham
*Attorney, Agent, or Firm*—Shlesinger Arkwright & Garver, LLP

[57] ABSTRACT

The invention concerns the use with the aim of antiviral prophylaxis of a current of carbon dioxide $CO_2$ in the supercritical state in contact with a tissue having a collagenous network of human or animal origin intended to be used as or in an implantable supporting tissue prosthesis as a biomaterial, wherein carbon dioxide in the supercritical state has the function of eliminating viral contamination from the tissue.

27 Claims, No Drawings

USES FOR A CURRENT OF SUPERCRITICAL CARBON DIOXIDE AS AN ANTIVIRAL AGENT

This application is a continuation-in-part of U.S. application Ser. No. 08/163,775, filed Dec. 9, 1993, now abandoned.

The invention concerns novel uses for carbon dioxide $CO_2$ in the supercritical state, within the context of the treatment of a tissue having a collagenous network (namely a bony, tendinous, cartilaginous or ligamentary tissue) of human or animal origin for obtaining a biomaterial implantable in the human body or in an animal body intended to be used as or in a supporting tissue prosthesis (bone, cartilage, tendon, ligament), that is to say incorporated into such a prosthesis or constituting such a prosthesis.

Carbon dioxide $CO_2$ in the supercritical state is known as such for various uses.

It will be recalled that fluids in the supercritical state may be defined as gases placed under conditions of temperature and pressure such that their properties are intermediate between those of gases and those of liquids. They are also called "dense gases" or "expanded liquids". For a given chemical substance, the precise point on the temperature-pressure diagram at which the two phases, liquid and vapor form only one phase is called the critical point. Beyond this critical temperature (Tc) and critical pressure (Pc), the fluid is in the so-called "supercritical" state.

Fluids in the supercritical state are known for their great ability to extract organic matter, particularly lipidic matter, from tissues.

Thus, EP-A-0.603.920 describes a process for the treatment of bone tissues in which a fluid in the supercritical state is made to penetrate all the bone tissue, which has the effect of extracting essentially lipidic organic matter and of reinforcing the mechanical strength. Other stages of the process are provided for obtaining implantable biomaterial, namely stages prior to mechanical cleaning and cutting, and subsequent stages of chemical treatment (with hydrogen peroxide) and/or enzyme treatment (protease) for extracting residual proteins, washing, dehydrating and disinfection in baths of ethanol (this last stage increasing safety as regards infection of the biomaterial on account of its virucidal properties).

Moreover, the processes used until now for limiting the risk of viral contamination of bone tissues (such as bones from bone banks) consist either of subjecting the tissue to gamma or beta radiation, or sterilizing it with ethylene oxide or by heat treatment.

Irradiation with gamma or beta rays does not enable all viruses to be destroyed with certainty. Indeed, certain viruses are radiation resistant. Moreover, this irradiation reduces the mechanical strength of bone, according to the radiation dose applied.

Sterilization with ethylene oxide presents the problem of the toxicity of this chemical compound, and of the product which it forms in the presence of water (ethylene glycol). Moreover, ethylene oxide modifies the bone structure and affects the osteoinduction properties.

Heat sterilization destroys the mechanical properties of collagen and hence of bone tissues.

Moreover, the mechanical destruction of microbial cells by sudden decompression in carbon dioxide $CO_2$ in the supercritical state has already been described ("Disruption of Microbial Cells by the Flash Discharge of High-Pressure Carbon Dioxide", Kozo Nakamura et al., Biosci. Biotech. Biochem., 58(7), 1297–1301, 1994).

Nevertheless, no prior document teaches that carbon dioxide $CO_2$ in the supercritical state could, in itself, have an antiviral effect within a tissue having a collagenous network such as bone tissue.

The inventors have now demonstrated, surprisingly, the novel antiviral function of carbon dioxide $CO_2$ in the supercritical state as regards these tissues.

The object of the invention is thus to propose novel uses for carbon dioxide in the supercritical state.

The aim of the invention is also to propose a process for the treatment of tissues having a collagenous network, particularly bone tissues, wherein the dioxide in the supercritical state is used in its viral inactivation function.

The object of the invention is moreover to propose a novel process for the antiviral prophylactic treatment of tissues having a collagenous network, and more particularly bone tissues, of human or animal origin, so as to obtain implantable biomaterials free from any viral contamination and capable of being used as supporting tissue protheses or in supporting tissue protheses.

In particular, the object of the invention is to propose a process for the antiviral treatment of bone tissue (such as bone tissue from a bone bank), before its implantation in the human body or in an animal body in a bone graft (allograft or xenograft), a process which ensures the elimination of any possible viral contamination and preserves, or even reinforces, the biomechanical properties of the bone tissue (strength, osteoinduction etc).

The invention thus concerns the use, with the aim of antiviral prophylaxis, of a current of carbon dioxide $CO_2$ in the supercritical state in contact with tissue having a collagenous network, of human or animal origin (and separated from the human or animal body) intended to serve as biomaterial, as an implantable supporting tissue prosthesis or in an implantable supporting tissue prosthesis, a use in which carbon dioxide in the supercritical state has a viral inactivation function, namely the elimination of viral contamination from the tissue.

The invention concerns the use as an antiviral agent of carbon dioxide in the supercritical state in contact with a tissue with a collagenous network able to withstand the conditions of pressure and temperature when carbon dioxide is in the supercritical state. The tissue with a collagenous network is in the solid phase, divided (into a powder) or undivided (in pieces or blocks) and is porous.

The invention also concerns the use, with the aim of antiviral prophylaxis, of a current of carbon dioxide $CO_2$ in the supercritical state in contact with a tissue with a collagenous network of animal or human origin intended to be used as or in an implantable supporting tissue thesis as biomaterial, at a rate of 100 to 500 grams, particularly of the order of 300 grams, of supercritical carbon dioxide per gram of tissue, with a collagenous network, to be treated.

The invention also concerns the use, with the aim of antiviral prophylaxis, of a current of carbon dioxide $CO_2$ in the supercritical state wherein the said current is left in contact with a tissue having a collagenous network of human or animal origin, intended to serve as implantable biomaterial as or in a supporting tissue prosthesis, for a period determined as a function of the flow rate of the said current so as to allow the passage of 100 to 500 grams, in particular of the order of 300 grams, of supercritical carbon dioxide per gram of tissue.

More particularly, the invention concerns the use of a current of supercritical carbon dioxide $CO_2$ as indicated above, in which the supercritical carbon dioxide is put under a pressure of between $1 \times 10^7$ Pa, and $5 \times 10^7$ Pa, in particular of the order of $2.5 \times 10^7$ Pa, and a temperature of between 40° C. and 55° C., in particular of the order of 50° C.

Thus, the invention concerns a process for the treatment, with the aim of antiviral prophylaxis, of a tissue having a collagenous network, in particular a bone tissue, of human or animal origin, intended to serve as a biomaterial as or in an implantable supporting tissue prosthesis (bone, cartilage, tendon or ligament), wherein it comprises at least one stage during which the tissue having a collagenous network is put into contact with a current of carbon dioxide $CO_2$ in the supercritical state which has the function of eliminating or preventing viral contamination within the tissue.

Thus, the invention concerns applications for carbon dioxide $CO_2$ in the supercritical state in which it can fulfil the function of an antiviral agent, namely the function of eliminating viral activity or preventing viral activity within a tissue having a collagenous network, of human or animal origin, such as a bone tissue.

The inventors have in point of fact demonstrated that when a tissue having a collagenous network, in particular a bone tissue, likely to be contaminated by viruses, is put into contact with a current of carbon dioxide in the supercritical state, this fluid fulfils the function of suppressing or preventing viral activity. Carbon dioxide in the supercritical state thus enables viruses to be combatted and provides an antiviral preventive treatment for tissues having a collagenous network, of human or animal origin, such as bone tissues.

No theoretical explanation can be given with certainty for the antiviral or virucidal effect of carbon dioxide in the supercritical state in tissues having a collagenous network. Nevertheless, it is probable that the molecule of carbon dioxide, having an organic nature, exhibits under supercritical conditions, on the one hand the ability to diffuse through all the porous material of tissue having a collagenous network, and on the other hand a strong biochemical reactivity with the organic molecules of biochemical compounds necessary for the development and activity of viruses (enzymes, protein constituents, capsids, nucleic acids, envelopes, etc.)

Moreover, the invention also concerns the use of carbon dioxide in the supercritical state in contact with a tissue having a collagenous network as indicated above jointly and in combination with at least one other stage selected from the following stages:

putting the tissue having a collagenous network into contact with a solution of hydrogen peroxide $H_2O_2$ having the function of eliminating viral contamination from the tissue, more particularly a solution of $H_2O_2$ the concentration by weight of which is greater than 1%, in particular of the order of 35%, and at a temperature of between 30° C. and 50° C., in particular of the order of 40° C., putting the tissue having a collagenous network into contact with a solution of sodium hydroxide NaOH having the function of eliminating viral contamination from the tissue, in particular a solution having a concentration by weight of between 3% and 15%, in particular of the order of 4%, of NaOH, preferably followed by one or more rinsings with water and neutralization by passage through a neutralizing solution, for example a solution of $NaH_2PO_4$, putting the tissue with a collagenous network into contact with a solution of ethanol $CH_3CH_2OH$ having the function of eliminating viral contamination from the tissue, in particular successively into a solution of ethanol, the volume concentration of which is greater than 90%, in particular of the order of 95%, then into a solution of ethanol having a concentration by volume greater than 95%, in particular of the order of 100%.

The invention also concerns a treatment process which comprises at least one of the stages mentioned above.

According to the invention, use is made of a treatment stage with a current of supercritical carbon dioxide $CO_2$ in the first instance, namely before carrying out the other stages described above with hydrogen peroxide, and/or sodium hydroxide and/or ethanol.

Advantageously and according to the invention, in order to put the tissue having a collagenous network into contact with the abovementioned solutions, the tissue is immersed in the said solution.

Advantageously, the following stages are carried out successively:

treatment by carbon dioxide $CO_2$ in the supercritical state, then treatment with hydrogen peroxide $H_2O_2$, then treatment with sodium hydroxide NaOH, then treatment with ethanol.

The succession of these stages guarantees in point of fact the elimination of any virus present and of any form of viral activity in the tissue treated.

The invention is more particularly applicable to combatting viruses of the family of Togaviridae, in particular of the genus Alphavirus, such as the Hepatitis C virus, and for preventing their transmission during tissue grafts; for combatting viruses of the family Picorviridae, in particular of the genus Enterovirus, more particularly the Polio Sabin virus, and preventing their transmission during tissue grafts; for combatting viruses of the family Herpesviridae and preventing their transmission during tissue grafts; for combatting viruses of the family Retroviridae, in particular of the genus Lentivirus, more particularly human HIV immunodeficiency viruses, and preventing their transmission during tissue grafts.

The following examples illustrate the invention.

EXPERIMENTAL PROTOCOL

In the examples, the capacity of each stage of the treatment to eliminate and/or inactivate viruses was tested:

1) by contaminating samples with a significant quantity of virus, then 2) carrying out the treatment stage under consideration on the samples, then 3) determining the quantity of virus eliminated and/or inactivated during this stage.

The samples tested were quarters of the head of a femur of human origin.

Experiments were carried out by the institut Pasteur (PARIS, FRANCE) according to protocol n° 5151-A1, and in accordance with French, American and OECD community regulations on Good Laboratory Practice.

For each experiment (namely for each stage tested and each virus) positive controls were carried out (virus stock with the same concentration as that used for contamination of the sample, immediately frozen at −75° C.; virus stock of the same concentration, ultracentrifuged, and an aliquot taken and frozen at −75° C.; virus stock of the same concentration, left at room temperature during the period of the experiment, then ultracentrifuged, and an aliquot taken and frozen at −75° C.; sample contaminated under the same conditions, the viral activity of which was immediately tested; sample contaminated under the same conditions, not subjected to the treatment stage but left under a hood at room temperature for the duration of the treatment stage, the viral activity of which was then tested) and negative controls (culture medium used for assays; sample put in the presence of a culture medium, then subjected to the treatment stage, the viral activity of which was then tested).

The viral activity of a bone sample was tested by a protocol, the reliability of which was previously verified on a sample of the same nature as those used in the treatment stage to be tested, and contaminated with a virus with an average resistance to physico-chemical treatments (porcine pseudorabies virus).

This protocol was as follows. The quarters of a femur head were cut into pieces and incubated in the culture medium for one hour at 4° C. An initial volume V1 of the supernatant was recovered. The pieces were then centrifuged at 400 g for 2 min and a second volume V2 of the supernatant was recovered. The mixture of the two volumes V1 +V2 of the supernatant was centrifuged at 1,550 g for 10 min to remove bone debris, the supernatant was ultracentrifuged, and an aliquot was taken and frozen at −75° C. The viral activity was assessed according to a standardized procedure for each virus, by determining the inverse transcriptase activity (for the HIV-1 virus), or by counting the lysis plaques on a monolayer cellular lawn (for the Sindbis, Polio Sabin 1 and porcine pseudorabies viruses). For the assay, aliquot parts were used, defrosted extemporaneously at 37° C. and placed in melting ice. A cytotoxicity control was carried out for each experiment. The detection limit was determined by the lowest theoretical titre obtained, or according to Poisson's formula if no viral production was observed. All the tests were carried out in duplicate.

In order to test the antiviral effect of stage n° 1 of the treatment with a current of carbon dioxide in the supercritical state, the procedure was as follows.

Drillings 4 mm in diameter and 1 to 1.5 cm deep were made in the bone blocks which were washed in two successive baths of 100 ml of the culture medium having 1% (v/v) of foetal calf serum, for 10 min with gentle agitation. The bone blocks were dried in an oven for 2 to 3 days, and the capacity was then tested of the drillings to retain liquids by introducing culture medium into them. If a leak was observed after 1 to 2 min, either the drilling was sealed with a biological cement, (for which the absence of an inactivating effect on viruses had been previously verified) or the sample was discarded. The samples retained were dried for an additional period of 2 to 3 days.

Each sample was then contaminated by introducing a viral suspension into the drillings which were then closed with a biological cement.

The contaminated samples were then treated with a current of carbon dioxide in the supercritical state for a period of 10 min per gram of sample. In order to do this, the process and device were used as described in EP-A-0.603.920.

Treatment stage n° 2 consisted of passage through a bath of a 35% (m/m) solution of hydrogen peroxide $H_2O_2$ at 40° C., the duration of which was determined by a flotation test (until the negative control sample sank).

In order to test the antiviral effect of stage n° 2, quarters of a femur head were used having been previously treated with supercritical carbon dioxide (10 min per gram of sample) as indicated above. The samples were washed in two successive baths of the culture medium and then dried for 24 h before being contaminated by adding 1 ml of the viral suspension (or of the culture medium for the negative control sample) drop by drop onto each of the faces of the sample. Penetration of the viral suspension into a sample was previously verified with a dye.

The viral activity was measured before and after treatment with hydrogen peroxide as indicated above.

Treatment stage n° 3 consisted of passage through a bath of 1M NaOH solution at 20° C. for 1 h, following by rinsing in water and neutralization by passage through a bath of $NaH_2PO_4$ (12 g/l) for 10 min. In order to test the antiviral effect of stage 3, quarters of a femur head were used having been previously treated successively with supercritical $CO_2$, and then with hydrogen peroxide $H_2O_2$ as indicated above.

The samples were then contaminated as indicated above for stage n° 2. The viral activity was measured before and after treatment with sodium hydroxide as indicated above.

Treatment stage n° 4 consisted of passage through a bath of 95% (v/v) ethanol for 3 h at room temperature followed by passage through a bath of 100% (v/v) ethanol for 2 h at room temperature.

To test the antiviral effect of stage n° 4, quarters of a femur head were used having been previously treated successively with supercritical $CO_2$, hydrogen peroxide and sodium hydroxide as indicated above. The samples were then contaminated as indicated for stage n° 2 and the viral activity was measured before and after treatment by stage n° 4 as indicated above.

From the experimental results, the reduction factor was calculated, for each treatment stage, represented by the logarithm to base 10 of the ratio between the total quantity of virus contaminating the sample before the treatment stage and the total quantity of virus contaminating the sample after the treatment stage. The reduction factor for the treatment stage is the sum of the logarithm to base 10 of the ratio of the total viral loading in the culture medium over the total viral loading in the sample before the treatment stage (if this logarithm is greater than 1) and the logarithm to base 10 of the ratio of the total viral loading in the sample before the treatment over the total viral loading in the sample after the treatment stage.

A treatment was inactivating on a virus above a reduction factor of 4, and was totally inactivating if the reduction factor was greater than 6.

Each test was considered as valid when the anticipated viral assay was obtained with the positive control (stock of virus of the same concentration immediately frozen) and if no plaque or no viral production was obtained with the negative controls.

EXAMPLE 1

The effect of antiviral treatment according to the invention was tested on the HIV-1 AIDS virus, which is a retrovirus with enveloped RNA of the family Retrovividae, sub-family Lentivirinae, genus Lentivirus, spherical and 80 to 130 nm in size, the genome of which consists of two identical single strand 9.2 kb RNA molecules. This virus is slightly resistant to physico-chemical treatments. It was obtained from supernatants of cultures of infected human cells.

TABLE 1

| | Stage n°1 | Stage n°2 | Stage n°3 | Stage n°4 | Total |
|---|---|---|---|---|---|
| Amount of virus introduced | $4.56 \cdot 10^7$ | $3.03 \cdot 10^6$ | $2.24 \cdot 10^7$ | $1.59 \cdot 10^7$ | — |
| Viral loading before treatment | $3.92 \cdot 10^5$ | $9.06 \cdot 10^3$ | $1.84 \cdot 10^4$ | $7.5 \cdot 10^5$ | — |
| Viral loading after treatment | <30 | <480 | <120 | <32 | — |
| Reduction factor | >4.12 | >1.28 | >2.19 | >4.37 | >11.96 |

In all cases the detection limit after treatment was not attained, no virus having been recovered. Consequently reduction factors were minimum values. The true values may have been considerably higher. Although no virus was detected after treatment, the reduction factors obtained in stages n° 2 and 3 were relatively low on account of the low viral loading before treatment, associated with an inactivating effect of the bone itself.

As will be seen, the viral inactivation effect of stage n° 1 was demonstrated. It will thus be noted that the effect of supercritical carbon dioxide was equivalent to that of alcohol. Moreover, the complete process (stages 1 to 4) had a reduction factor greater than 11.96, and was thus completely inactivating as regards the virus.

EXAMPLE 2

The effect of the antiviral treatment of the invention was tested on the Sindbis virus, which is a togavirus with enveloped RNA. This virus is considered as a model for that of Hepatitis C which is, after AIDS, the second most menacing infectious disease for public health within the context of risks associated with tissue grafts. This virus belongs to the family of Togaviridae, genus Alphavirus. It is a spherical virus with a diameter of 60 to 70 nm. Its genome consists of a single strand 12 kb RNA molecule. It is weakly resistant to physico-chemical treatments. It was obtained from supernatants of a culture of infected monkey renal cells.

The following Table 2 gives the results obtained.

TABLE 2

|  | Stage n°1 | Stage n°2 | Stage n°3 | Stage n°4 | Total |
|---|---|---|---|---|---|
| Amount of virus introduced | $1.75 \; 10^7$ | $6.05 \; 10^6$ | $9.47 \; 10^6$ | $1.09 \; 10^7$ | — |
| Viral loading before treatment | $2.24 \; 10^5$ | $2.93 \; 10^6$ | $4.17 \; 10^5$ | $3.81 \; 10^6$ | — |
| Viral loading after treatment | <10 | <9 | 28 | 32 | — |
| Reduction factor | >4.34 | >5.52 | 4.17 | 5.08 | >19.11 |

In stages n° 1 and n° 2, the detection limit after treatment was not attained, no virus having been recovered. Consequently reduction factors were minimum values. The true values may have been considerably higher. It was also noted that the complete process (stages 1 to 4) had a reduction factor greater than 19.11, and was thus total inactivating as regards the virus.

EXAMPLE 3

The effect of the antiviral treatment according to the invention was tested on the Polio Sabin 1 virus, which is a picornavirus with non-enveloped RNA. Like all non-enveloped viruses, it is more resistant to physico-chemical treatments than enveloped viruses. This virus belongs to the family Picornaviridae, genus Enterovirus. It is non-enveloped virus with icosahedral symmetry, 28 to 30 nm in diameter. Its genome consists of a positive polarity single strand 7.4 kb RNA molecule. Its resistance to physico-chemical treatments is medium to strong. It was obtained from supernatants of a culture of infected human cells.

The following Table 3 gives the results obtained.

TABLE 3

|  | Stage n°1 | Stage n°2 | Stage n°3 | Stage n°4 | Total |
|---|---|---|---|---|---|
| Amount of virus introduced | $1.00 \; 10^8$ | $7.01 \; 10^7$ | $7.20 \; 10^7$ | $5.41 \; 10^7$ | — |
| Viral loading before treatment | $6.90 \; 10^7$ | $2.21 \; 10^8$ | $5.65 \; 10^7$ | $6.66 \; 10^7$ | — |
| Viral loading after treatment | <17 | <16 | $1.94 \; 10^3$ | <16 | — |
| Reduction factor | >6.60 | >7.14 | 4.46 | >6.61 | >24.81 |

In the case where the figure for the viral loading is preceded by the sign <, the detection limit after treatment was not reached, no virus having been recovered. Consequently the corresponding reduction factors are minimum values. The true values may be considerably greater.

It will again be noted that supercritical carbon dioxide inactivated this virus, in a manner equivalent to treatment with ethanol. Moreover, the complete treatment (stages 1 to 4) had a reduction factor >24.81, and was thus completely inactivating as regards the virus.

EXAMPLE 4

The effect of the antiviral treatment according to the invention was tested on the porcine pseudorabies virus, which is a herpesvirus with an enveloped DNA. This virus belongs to the family Herpesviridae, sub-family alphaherpesvirinae, genus Varicellavirus. It is an enveloped virus, with an icosahedral symmetry, the size of which varies from 100 to 200 nm. Its genome consists of a linear double strand 150 to 200 kb DNA molecule. It has average resistance to physico-chemical treatments. It was obtained from supernatants of a culture of fibroblasts from infected rabbit embryos.

The following Table 4 gives the results obtained.

TABLE 4

|  | Stage n°1 | Stage n°2 | Stage n°3 | Stage n°4 | Total |
|---|---|---|---|---|---|
| Amount of virus introduced | $1.04 \; 10^7$ | $5.65 \; 10^6$ | $1.01 \; 10^7$ | $1.02 \; 10^7$ | — |
| Viral loading before treatment | $1.36 \; 10^5$ | $8.40 \; 10^5$ | $3.76 \; 10^5$ | $1.5 \; 10^5$ | — |
| Viral loading after treatment | <13 | <8 | <8 | <9 | — |
| Reduction factor | >4.03 | >5.00 | >4.66 | >4.22 | >17.91 |

In all cases the detection limit after treatment was not attained, no virus having been recovered. Consequently reduction factors were minimum values. The true values may have been considerably higher. Here again, treatment with supercritical carbon dioxide inactivated this virus and the complete process had a reduction factor (greater than 17.91) which ensured elimination of all viral contamination.

Examples 1 to 4 above demonstrate the antiviral effect of supercritical carbon dioxide and of stages 1 to 4 on various reference viruses respectively (virus with RNA or with DNA, enveloped or not, resistant or not to physico-chemical treatments etc), under standardized conditions and hence the effectiveness of the invention against viruses. In point of fact, the viruses tested were chosen in accordance with European regulations on viral validations (Guideline III/8115/89) and on blood derivatives (Guideline III/83179/89).

We claim:

1. A method of using carbon dioxide in supercritical state for eliminating viral contamination from an implantable tissue, comprising the steps of:
   a) treating the tissue with a predetermined amount of supercritical carbon dioxide;
   b) treating the tissue obtained in step a) with hydrogen peroxide;
   c) treating the tissue obtained in step b) with sodium hydroxide; and
   d) treating the tissue obtained in step c) with ethanol.

2. A method of using carbon dioxide in supercritical state for eliminating vital contamination from an implantable tissue, comprising the steps of:
   a) treating the tissue with a predetermined amount of supercritical carbon dioxide; and
   b) treating the tissue with a predetermined amount of sodium hydroxide solution.

3. The method as claimed in claim 2, wherein:
   a) the tissue is treated at a rate of about 100 to about 500 grams of supercritical carbon dioxide/gram of tissue.

4. The method as claimed in claim 2, wherein:
   a) the tissue is treated at a rate of about 300 grams of supercritical carbon dioxide/gram of tissue.

5. The method as claimed in claim 2, and wherein:
   a) the tissue is treated with carbon dioxide for a period determined as a function of carbon dioxide flow rate in order to permit passage of about 100 to about 500 grams of supercritical carbon dioxide/gram of tissue.

6. The method as claimed in claim 2, and wherein:
   a) the tissue is treated with carbon dioxide for a period determined as a function of carbon dioxide flow rate in order to permit passage of about 300 grams of supercritical carbon dioxide/gram of tissue.

7. The method as claimed in claim 2, wherein:
   a) the supercritical carbon dioxide is applied at a pressure between about $1\times10^7$ Pa and about $5\times10^7$ Pa.

8. The method as claimed in claim 7, wherein:
   a) the supercritical carbon dioxide is applied at a pressure between about $2.5\times10^7$ Pa.

9. The method as claimed in claim 2, wherein:
   a) the supercritical carbon dioxide is applied at a temperature between about 40° C. and about 55° C.

10. The method as claimed in claim 9, wherein:
    a) the supercritical carbon dioxide is applied at a temperature about 50° C.

11. The method as claimed in claim 2, further comprising the step of:
    a) treating the tissue with a predetermined amount of hydrogen peroxide to further eliminate vital contamination from the tissue.

12. The method as claimed in claim 11, wherein:
    a) the hydrogen peroxide has a concentration of about 1% to about 35% by weight.

13. The method as claimed in claim 11, wherein:
    a) the hydrogen peroxide has a concentration of about 35% by weight.

14. The method as claimed in claim 11, and wherein:
    a) the tissue is treated at a temperature of about 30° C. to about 50° C.

15. The method as claimed in claim 11, and wherein:
    a) the tissue is treated at a temperature of about 40° C.

16. The method as claimed in claim 2, further comprising the step of:
    a) treating the tissue with a predetermined amount of ethanol to further eliminate a viral contamination from the tissue.

17. The method as claimed in claim 16, wherein:
    a) the ethanol has a concentration greater than about 90% by volume.

18. The method as claimed in claim 16, wherein:
    a) the ethanol has a concentration about 95% by volume.

19. The method as claimed in claim 17, further comprising the step of:
    a) immersing the ethanol treated tissue in another ethanol solution with a concentration greater than about 95% by volume.

20. The method as claimed in claim 17, further comprising the step of:
    a) immersing the ethanol treated tissue in another ethanol solution with a concentration of about 100% by volume.

21. The method as claimed in claim 2, wherein:
    a) the viral contamination is a virus selected from the family group consisting of Togaviridae, Picoviridae, Herpesviridae and Retroviridae.

22. The method as claimed in claim 21, wherein:
    a) the viral contamination is a virus selected from the genus group consisting of Alphavirus, Enterovirus and Lentivirus.

23. The method as claimed in claim 22, wherein:
    a) the virus is selected from the group consisting of herpes virus, human immunodeficiency virus (HIV), Hepatitis C virus, and Polio sabin virus.

24. The method as claimed in claim 2, wherein:
    a) the tissue is selected from the group consisting of bone, cartilage, tendon and ligament.

25. A method of using carbon dioxide in supercritical state for eliminating viral contamination from an implantable tissue, comprising the steps of:
    a) treating the tissue with a predetermined amount of supercritical carbon dioxide;
    b) treating the tissue with a predetermined amount of sodium hydroxide solution; and
    c) the sodium hydroxide has a concentration between about 3% and 15%.

26. A method of using carbon dioxide in supercritical state for eliminating viral contamination from an implantable tissue, comprising the steps of:
    a) treating the tissue with a predetermined amount of supercritical carbon dioxide;
    b) treating the tissue with a predetermined amount of sodium hydroxide solution; and
    c) the sodium hydroxide has a concentration of about 4%.

27. A method of using carbon dioxide in supercritical state for eliminating viral contamination from an implantable tissue, comprising the steps of:

a) treating the tissue with a predetermined amount of supercritical carbon dioxide;

b) treating the tissue with a predetermined amount of sodium hydroxide solution;

c) rising the tissue with water;

d) immersing the rinsed tissue in a neutralizing solution; and e) the rinsing and immersing steps are carried out subsequent to treating the tissue with sodium hydroxide.

* * * * *